US010045960B2

(12) United States Patent
Yamashita et al.

(10) Patent No.: US 10,045,960 B2
(45) Date of Patent: *Aug. 14, 2018

(54) COATING COMPOSITION AND MEDICAL DEVICE

(71) Applicant: TERUMO KABUSHIKI KAISHA, Shibuya-ku, Tokyo (JP)

(72) Inventors: Keiko Yamashita, Kanagawa (JP); Shigenori Nozawa, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/421,645

(22) Filed: Feb. 1, 2017

(65) Prior Publication Data

US 2017/0143663 A1    May 25, 2017

Related U.S. Application Data

(63) Continuation of application No. 14/496,058, filed on Sep. 25, 2014, now Pat. No. 9,603,974, which is a (Continued)

(30) Foreign Application Priority Data

Mar. 27, 2012  (JP) ................................. 2012-071668
Jan. 25, 2013  (JP) ................................. 2013-012180

(51) Int. Cl.
*A61K 31/10* (2006.01)
*A61K 31/337* (2006.01)
(Continued)

(52) U.S. Cl.
CPC .............. *A61K 31/337* (2013.01); *A61F 2/93* (2013.01); *A61K 47/10* (2013.01); *A61K 47/183* (2013.01);
(Continued)

(58) Field of Classification Search
None
See application file for complete search history.

(56) References Cited

U.S. PATENT DOCUMENTS 5,102,402 A    4/1992  Dror et al.
6,268,390 B1    7/2001  Kunz
(Continued)

FOREIGN PATENT DOCUMENTS

CN    1956742 A    5/2007
CN    101610798 A    12/2009
(Continued)

OTHER PUBLICATIONS

Thomas et al. (Vasodilatory Properties of mono-L-arginine-containing compounds, Biochemical and Biophysical Research Communications, vol. 154, No. 1, 1988, pp. 332-338.*
(Continued)

*Primary Examiner* — Robert A Wax
*Assistant Examiner* — Melissa S Mercier
(74) *Attorney, Agent, or Firm* — Buchanan, Ingersoll & Rooney PC

(57) ABSTRACT

A coating composition for drug-eluting medical devices, which enables a medical device to be delivered to a target tissue for the purpose of treating an affected blood vessel part such as restenosis, without easy separation of a drug from the medical device during the delivery process is provided. The coating composition for drug-eluting medical devices contains a water-insoluble drug and at least one selected from the group consisting of ester compounds of amino acids, which have a hydropathy index of the amino acid of zero or less than zero, and salts thereof. A drug coating layer, a drug-eluting medical device and a method of treatment are also provided.

15 Claims, 3 Drawing Sheets

Related U.S. Application Data continuation of application No. PCT/JP2013/057495, filed on Mar. 15, 2013.

(60) Provisional application No. 61/721,725, filed on Nov. 2, 2012.

(51) Int. Cl.
| | | |
|---|---|---|
| A61L 29/08 | (2006.01) | |
| A61L 29/16 | (2006.01) | |
| A61L 31/10 | (2006.01) | |
| A61L 31/16 | (2006.01) | |
| A61F 2/93 | (2013.01) | |
| A61L 29/14 | (2006.01) | |
| A61L 31/08 | (2006.01) | |
| A61L 31/14 | (2006.01) | |
| A61M 25/10 | (2013.01) | |
| A61K 47/10 | (2017.01) | |
| A61K 47/18 | (2017.01) | |

(52) U.S. Cl.
CPC .............. *A61L 29/08* (2013.01); *A61L 29/085* (2013.01); *A61L 29/143* (2013.01); *A61L 29/16* (2013.01); *A61L 31/08* (2013.01); *A61L 31/10* (2013.01); *A61L 31/143* (2013.01); *A61L 31/16* (2013.01); *A61M 25/10* (2013.01); *A61F 2310/0097* (2013.01); *A61F 2310/00976* (2013.01); *A61L 2300/416* (2013.01); *A61L 2420/06* (2013.01); *A61M 2025/105* (2013.01)

(56) References Cited

U.S. PATENT DOCUMENTS

| | | |
|---|---|---|
| 7,803,149 B2 | 9/2010 | Bates et al. |
| 7,811,622 B2 | 10/2010 | Bates et al. |
| 8,172,793 B2 | 5/2012 | Bates et al. |
| 8,241,249 B2 | 8/2012 | Wang |
| 8,244,344 B2 | 8/2012 | Wang |
| 8,257,305 B2 | 9/2012 | Speck et al. |
| 8,366,660 B2 | 2/2013 | Wang |
| 8,366,662 B2 | 2/2013 | Wang |
| 8,403,910 B2 | 3/2013 | Wang |
| 8,404,300 B2 | 3/2013 | Wang |
| 8,414,525 B2 | 4/2013 | Wang |
| 8,414,526 B2 | 4/2013 | Wang |
| 8,414,909 B2 | 4/2013 | Wang |
| 8,414,910 B2 | 4/2013 | Wang |
| 8,425,459 B2 | 4/2013 | Wang |
| 8,439,868 B2 | 5/2013 | Speck et al. |
| 2006/0134166 A1 | 6/2006 | Luthra et al. |
| 2008/0021385 A1 | 1/2008 | Barry et al. |
| 2009/0136560 A1 | 5/2009 | Bates et al. |
| 2010/0179475 A1 | 7/2010 | Hoffmann et al. |
| 2010/0209472 A1* | 8/2010 | Wang .................. A61K 31/337 424/423 |
| 2011/0015725 A1 | 1/2011 | Bates et al. |
| 2011/0160698 A1 | 6/2011 | Hoffmann et al. |
| 2011/0196340 A1 | 8/2011 | Barry et al. |
| 2011/0238011 A1 | 9/2011 | Scheller et al. |
| 2011/0295200 A1 | 12/2011 | Speck et al. |
| 2011/0300221 A1 | 12/2011 | Kunz et al. |
| 2012/0239001 A1 | 9/2012 | Barry et al. |
| 2013/0189190 A1 | 7/2013 | Wang |
| 2013/0189329 A1 | 7/2013 | Wang |
| 2013/0197431 A1 | 8/2013 | Wang |
| 2013/0197434 A1 | 8/2013 | Wang |
| 2013/0197435 A1 | 8/2013 | Wang |
| 2013/0197436 A1 | 8/2013 | Wang |
| 2013/0209662 A1 | 8/2013 | Wang et al. |
| 2013/0231638 A1 | 9/2013 | Speck et al. |
| 2014/0005541 A1 | 1/2014 | Bates et al. |
| 2014/0227192 A1 | 8/2014 | Speck et al. |
| 2014/0227193 A1 | 8/2014 | Speck et al. |
| 2014/0227194 A1 | 8/2014 | Speck et al. |
| 2014/0228750 A1 | 8/2014 | Speck et al. |
| 2014/0228751 A1 | 8/2014 | Speck et al. |
| 2014/0228752 A1 | 8/2014 | Speck et al. |

FOREIGN PATENT DOCUMENTS

| | | |
|---|---|---|
| JP | 4-270227 A | 9/1992 |
| JP | 8-27002 A | 1/1996 |
| JP | 2008-502376 A | 1/2008 |
| JP | 2008-509722 A | 4/2008 |
| JP | 2010-509991 A | 4/2010 |
| JP | 2010-516307 A | 5/2010 |
| JP | 2010-540159 A | 12/2010 |
| WO | WO 2005/115492 A1 | 12/2005 |
| WO | WO 2006/022754 A2 | 3/2006 |
| WO | WO 2008/063576 A2 | 5/2008 |
| WO | WO 2008/086794 A2 | 7/2008 |
| WO | WO 2009/051614 A1 | 4/2009 |

OTHER PUBLICATIONS

International Search Report (PCT/ISA/210) dated May 28, 2013, by the Japanese Patent Office as the International Searching Authority for International Application No. PCT/JP2013/057495.

Byeong-Su Kim et al., "MAD (Multiagent Delivery) Nanolayer: Delivering Multiple Therapeutics From Hierarchically Assembled Surface Coatings", Langmiur Article, American Chemical Society, 2009, vol. 25, No. 24, pp. 14086-14092.

George Thomas et al., "Effect of Nα-Benzoyl-L-Arginine Ethyl Ester on Coronary Perfusion Pressure in Isolated Guinea Pig Heart", European Journal of Pharmacology, 1990, vol. 178, No. 2, pp. 251-254.

Michael Y. Farhat et al., "Endothelium-Mediated Effects of N-Substituted Arginines on the Isolated Perfused Rat Kidney", The Journal of Pharmacology and Experimental Therapeutics, 1990, vol. 255, No. 2, pp. 473-477.

Michael Y. Farhat et al., "Vasodilatory Property of N-Alpha Benzoyl-L-Arginine Ethyl Ester in the Rat Isolated Pulmonary Artery and Perfused Lung", The Journal of Pharmacology and Experimental Therapeutics, 1990, vol. 254, No. 1, pp. 289-293.

George Thomas et al. "Vasodilatory Properties of Mono-L-Arginine-Containing Compounds", Biochemical and Biophysical Research Communications, Jul. 15, 1988, vol. 154, No. 1, pp. 332-338.

Office Action dated May 29, 2015, by the Chinese Patent Office in corresponding Chinese Patent Application No. 201380015727.0 (11 pages).

The Extended European Search Report dated Jul. 14, 2015, by the European Patent Office in corresponding European Patent Application No. 13768084.9-1455 (9 pages).

Office Action dated Sep. 23, 2015, by the Canadian Intellectual Property Office in corresponding Canadian Patent Application No. 2,867,429 (3 pages).

Office Action (Patent Examination Report No. 1) dated Oct. 1, 2015, by the Australian Patent Office in corresponding Australian Patent Application No. 2013238160 (4 pages).

Office Action issued by the Russian Patent Office in corresponding Russian Patent Application No. 2014143070 dated Dec. 10, 2015 (12 pages including English translation).

Office Action issued by the Russian Patent Office in corresponding Russian Patent Application No. 2014143070 dated Jun. 3, 2016 (6 pages including English translation).

Thomas et al., "Vasodilatory Properties of Mono-L-Arginine-Containing Compounds, Biochemical and Biophysical Research Communications", vol. 154, No. 1, 1988, pp. 332-338.

Database CA [Online] Chemical Abstracts Service, Columbus,Ohio, US; XP002741705, retrieved from STN-International accession No. 124:270566 CA Database accession No. 124:270566 *abstract * Database WPI Week 199614.

Thomson Scientific, London, GB; AN 1996-136188 XP002741706, & JP H08 27002 A (Sankyo Co Ltd), Jan. 30, 1996 (Jan. 30, 1996)

(56) References Cited

OTHER PUBLICATIONS abstract *& Database EP0D0C * European Patent Office, The Hague, NL; (Corresponds to JPH 08 27002 previously cited on Feb. 1, 2017).
XP002741707, Database accession No. JP-16775894-A *abstract* & JP H08 27002 A (Sankyo Co) Jan. 30, 1996 (Jan. 30, 1996) (Corresponds to JPH 08 27002 previously cited on Feb. 1, 2017).
Database CA [Online] Chemical Abstracts Service, Columbus, Ohio, US; XP002741708, retrieved from STN-International accession No. 118:66849 Database accession No. 118:66849 *abstract* Database WPI Week 199245.
XP002741709, & JP H04 270227 A (Yamanouchi Pharm Co Ltd) Sep. 25, 1992 (Sep. 25, 1992) * abstract * -& Database EPODOC European Patent Office, The Hague, NL; XP002741710,(Corresponds to JP 04270227 previously cited on Feb. 1, 2017).
XP002741710, Database accession No. JP-11569191-A & JP H04 270227 A (Yamanouchi Pharma Co Ltd) Sep. 25, 1992 (Sep. 25, 1992) (Corresponds to JP 04270227 previously cited on Feb. 1, 2017).

* cited by examiner

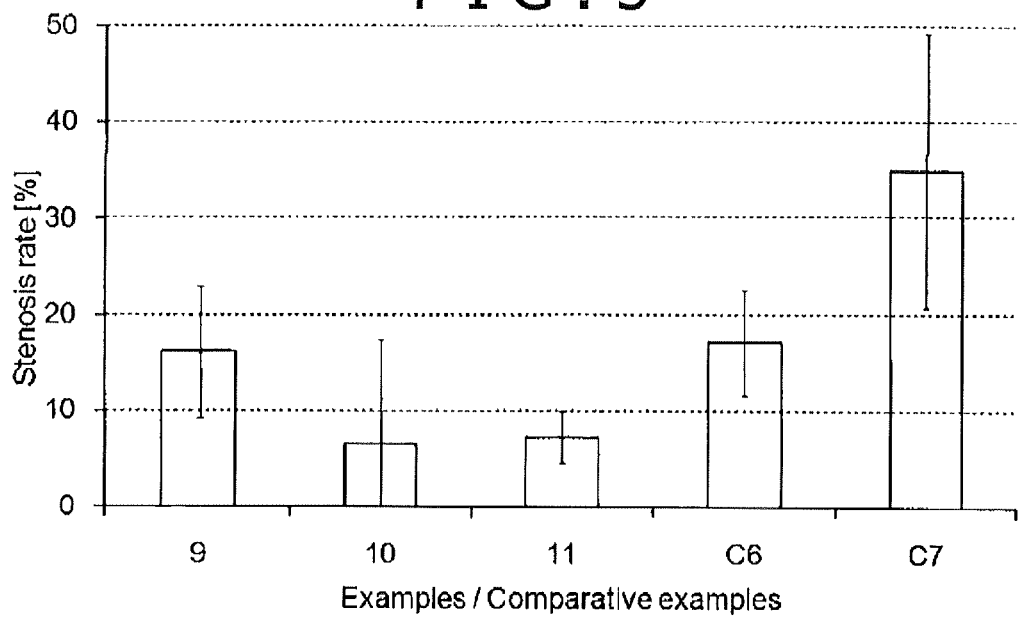

COATING COMPOSITION AND MEDICAL DEVICE

RELATED APPLICATIONS

This application is a continuation of U.S. patent application Ser. No. 14/496,058, filed Sep. 25, 2014, which claims priority as a continuation application under 35 U.S.C. § 120 to International Application No. PCT/JP2013/057495 filed on Mar. 15, 2013, designating the U.S., and which claims priority to Japanese Application No. 2012-071668 filed on Mar. 27, 2012, Japanese Application No. 2013-012180 filed on Jan. 25, 2013, and U.S. Provisional Application No. 61/721,725, filed Nov. 2, 2012, the entire contents of which are incorporated herein by reference.

TECHNICAL FIELD

Disclosed is a coating composition for a drug-eluting medical device, a drug coating layer of a drug-eluting medical device and/or a drug-eluting medical device coated with the coating composition.

BACKGROUND DISCUSSION

As an example of local drug delivery therapy, there has been a drug-eluting stent (DES). The DES is so designed as to locally release a drug in a sustained manner for a long period of time, thereby preventing restenosis of a blood vessel. The sustained release of a drug from the DES is achieved by a polymer conjugate such as polylactic acid (PLA). In this case, since the polymer remains in a living body for a long period of time, there is a problem of severe complications such as chronic inflammation or delayed thrombosis at the affected part of a lesion.

Conventionally, it has been reported that sustained release of a drug for a long period of time is necessary for restraining restenosis. In recent years, however, it has been being made clear that by rapid transfer of a drug to a target tissue, even a short-term sustained drug effect is sufficient for successfully preventing restenosis. The technology of rapid drug delivery does not need a polymer matrix, such as PLA (polylactic acid) or PLGA (polylactic acid-glycolic acid copolymer), for sustained release, and is therefore advantageous for avoiding complications.

Besides, in recent years, development of DEBs (Drug Eluting Balloons) wherein a balloon catheter is coated with a drug has been made positively, and it has been reported to be effective in treating and preventing restenosis. The balloon is coated with a coating that contains a drug and additives, and, when a blood vessel is dilated, the balloon is pressed against the blood vessel wall so as to deliver the drug to the target tissue.

SUMMARY

If the drug is easily peeled from the balloon in the process of delivery of the balloon to the target tissue, the amount of the drug remaining on the balloon would be reduced to below a sufficient level for a therapeutic effect before the balloon is delivered to the affected part of lesion. In such a situation, the expected therapeutic effect cannot be promised. In addition, the drug easily peeled off during the delivery process is unnecessarily exposed to the blood, which is undesirable from the viewpoint of safety. Thus, there is a need for a drug coating layer which ensures that a balloon catheter coated with a drug can be delivered to an affected part of lesion without peeling of the drug, the balloon can be pressed against a blood vessel wall simultaneously with expansion, and the drug can thereby be released rapidly.

If a low-molecular compound used in the coating together with the drug is excessively hydrophobic, its hydrophobic interaction with the water-insoluble drug would be strong, and the hydrophobic regions of them would have a high affinity for the balloon surface. As a result, release (transfer) of the drug from the balloon to the affected part (the inner surface of the blood vessel) would not easily occur, even upon contact of the balloon with the affected part. Furthermore, if the hydrophobicity of the low-molecular compound mixed with the hydrophobic drug is strong, the hydrophobic interaction between molecules of the water-insoluble drug would be so strong that the drug may easily aggregate on the surface of the medical device, making it difficult to achieve a uniform coating. In addition, the drug applied to the medical device surface in an aggregated state would be easily detached from the balloon surface during handling, which is undesirable from the viewpoints of safety and function. If the low-molecular compound is excessively hydrophilic, on the other hand, it may be difficult for the compound to be mixed with the water-insoluble drug. In such a case, it may be difficult to prepare a stable drug coating layer solution, or the low-molecular compound may be easily dissolved by the bloodstream together with the drug, due to the strong hydrophilicity thereof. Therefore, the low-molecular compound used in the coating together with the drug is desired to have both a hydrophilic region for relaxing the hydrophobic interaction between the molecules of the water-insoluble drug and ensuring uniform dispersion of the drug and a hydrophobic region that has an affinity for the water-insoluble drug. In short, the balance between the hydrophilic region and the hydrophobic region is important.

BRIEF DESCRIPTION OF DRAWINGS

In FIG. 1, reference numeral 1 is an imitative blood vessel, reference numeral 2 is a guiding catheter, reference numeral 3 is a balloon catheter, and reference numeral 4 is a balloon.

FIG. 5 is a graph representing the stenosis rate in Examples 9 to 11 and Comparative Examples C6 and C7, in an evaluation of the effectiveness in a swine coronary artery.

DETAILED DESCRIPTION

Figure 1:
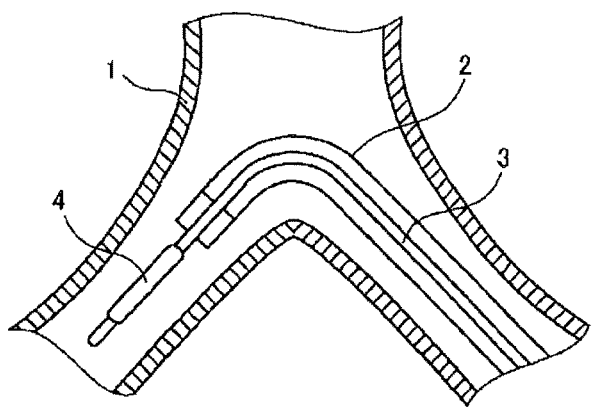
FIG. 1 is a schematic sectional view of an experimental apparatus used in a drug coating layer durability evaluation test using an imitative blood vessel, in a state in which a balloon catheter is inserted in a guiding catheter disposed in the imitative blood vessel.

According to an illustrative aspect, disclosed is a coating composition for drug-eluting medical devices which ensures that a drug can be delivered for treatment of an affected blood vessel part such as restenosis, without easy peeling of the drug from the medical device in the process of delivery to a target tissue, that the drug can be rapidly released at the affected part of lesion after the delivery, and that transferability of the drug to the target tissue can be enhanced.

It has been determined that when a coating composition containing a water-insoluble drug and at least one selected from the group consisting of ester compounds of amino acids, which have a hydropathy index (hydrophobicity index: HI) of the amino acid of zero or less than zero, and salts thereof is used, it is possible to form a drug coating layer on a surface of a medical device, the drug coating layer ensuring that the drug can be delivered for treatment of an affected blood vessel part such as restenosis, without easy peeling of the drug from the medical device during the process of delivery to the target tissue.

Disclosed are the following aspects (1) to (13).

(1) A coating composition for a drug-eluting medical device, containing a water-insoluble drug and at least one selected from the group consisting of ester compounds of amino acids, which have a hydropathy index of the amino acid of zero or less than zero, and salts thereof.

(2) The coating composition according to the above paragraph (1), wherein the amino acid is an α-amino acid.

(3) The coating composition according to the above paragraph (1) or (2), wherein the ester compound is an ester compound of at least one amino acid and a monohydric alcohol of up to five carbon atoms, the at least one amino acid being selected from the group consisting of glycine, serine, asparagine, aspartic acid, glutamine, glutamic acid, arginine, threonine, histidine, lysine, tyrosine, tryptophan, amino acids obtained by replacing at least one of hydrogen atoms of an amino group at the α-position in the above-mentioned amino acids with an alkyl group of up to five carbon atoms, a benzyl group or a benzoyl group, proline and amino acids obtained by replacing a hydrogen atom of an imino group of proline with an alkyl group of up to five carbon atoms, a benzyl group or a benzoyl group.

(4) The coating composition according to any of the above paragraphs (1) to (3), wherein the ester compound is represented by the following formula:

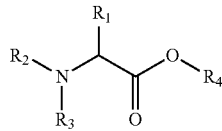

where $R_1$ is a hydrogen atom, guanidinopropyl group, carbamoylmethyl group, carboxymethyl group, methoxycarbonylmethyl group, ethoxycarbonylmethyl group, 2-carbamoylethyl group, 2-carboxyethyl group, 2-methoxycarbonylethyl group, 2-ethoxycarbonylethyl group, (1H-imidazol-4-yl)methyl group, 4-aminobutyl group, hydroxymethyl group, 1-hydroxyethyl group, (1H-indol-3-yl)methyl group or 4-hydroxybenzyl group or forms a trimethylene group together with $R_2$, $R_2$ is a hydrogen atom or forms a trimethylene group together with $R_1$, $R_3$ is a hydrogen atom, an alkyl group of up to five carbon atoms, benzyl group or benzoyl group, and $R_4$ is an alkyl group of up to five carbon atoms.

(5) The coating composition according to any of the above paragraphs (1) to (4), wherein the ester compound is at least one selected from the group consisting of benzylglycine ethyl ester, benzylglycine methyl ester, arginine ethyl ester, arginine methyl ester, benzoylarginine ethyl ester, benzoylarginine methyl ester, diethyl aspartate, methyl aspartate, dimethyl aspartate, glycine ethyl ester, glycine methyl ester, serine ethyl ester and serine methyl ester.

(6) The coating composition according to any of the above paragraphs (1) to (5), further containing a lower alcohol.

(7) The coating composition according to the above paragraph (6), wherein the lower alcohol is glycerine.

(8) The coating composition according to any of the above paragraphs (1) to (7), wherein the water-insoluble drug is at least one selected from the group consisting of paclitaxel, rapamycin, docetaxel and everolimus.

(9) The coating composition according to any of the above paragraphs (1) to (8), wherein the medical device is a medical device which is radially expandable in a lumen.

(10) The coating composition according to the above paragraph (9), wherein the medical device which is radically expandable in the lumen is a balloon catheter or a stent.

(11) A drug coating layer which is formed on at least part of a surface of a medical device by the coating composition according to any of the above paragraphs (1) to (10).

(12) A drug-eluting medical device having an outer surface coated with the coating composition according to any of the above paragraphs (1) to (10).

(13) A method of treatment, including a step of delivering the medical device according to the above paragraph (12) into a lumen, a step of radially expanding the medical device in the lumen and a step of eluting a drug from a drug coating layer formed on at least part of the surface of the medical device, and allowing the drug to act on the lumen.

According to the disclosed aspects, it is possible to provide a coating composition for drug-eluting medical devices which ensures that a drug can be delivered for treatment of an affected blood vessel part such as restenosis, without easy peeling of the drug from a medical device in the process of delivery to the target tissue, that the drug can be rapidly released at the affected part of lesion after the delivery, and that transferability of the drug to the target tissue can be enhanced.

1. Coating Composition

The coating composition is a coating composition for drug-eluting medical devices, which contains a water-insoluble drug and at least one selected from the group consisting of ester compounds of amino acids, which have a hydropathy index of the amino acid of zero or less than zero, and salts thereof.

The coating composition contains the water-insoluble drug and at least one selected from the group consisting of the ester compounds of amino acids, which have a hydropathy index of the amino acid of zero or less than zero, and salts thereof, is a blend having the ingredients blended with each other, and is a non-polymeric coating. These ingredients are not bonded to each other by a covalent bond.

The coating composition is preferably applied uniformly, to be restrained from separation during the delivery to an affected part, and to release the drug efficiently at the affected part. Therefore, it is preferable that the low-molecular compound blended with the water-insoluble drug is miscible with water and water-miscible organic solvents and has an affinity also for the hydrophobic water-insoluble drug. From this point of view, the low-molecular compound is preferably an ester compound of an amino acid that has a hydropathy index of zero or less than zero and/or salts thereof.

On the other hand, for example, a citric acid ester or the like has three carboxyl groups in one molecule thereof, and esterification of the carboxyl group portion is supposed to significantly lower the polarity of the citric ester or the like. As a result, although the affinity of the citric ester or the like for the water-insoluble drug is enhanced, the citric ester or the like is lowered in polarity and strengthened in hydrophobic interaction with the water-insoluble drug, so that the molecules of the drug are liable to aggregate. In addition, it becomes difficult for the drug to be released from the balloon surface at the affected part. Thus, it is supposed that a favorable coating composition cannot be obtained.

(1) Water-Insoluble Drug

The water-insoluble drug means a drug which is insoluble or difficultly soluble in water, specifically a drug which has a solubility in water of less than 5 mg/mL at pH 5 to 8. The solubility may be less than 1 mg/mL, or may further be less than 0.1 mg/mL. The water-insoluble drug includes fat-soluble drugs.

Preferable examples of the water-insoluble drug include immunosuppressants, e.g., cyclosporins inclusive of cyclosporin, immunoadjuvants such as rapamycin, etc., carcinostatics such as paclitaxel, etc., antiviral or antibacterial agents, antineoplastic agents, analgesic and anti-inflammatory agents, antibiotics, antiepileptics, anxiolytic agents, antiparalytic agents, antagonists, neuron blocking agents, anticholinergic and cholinergic agents, muscarine antagonists and muscarine agents, antiadrenergic agents, antiarrhythmic agents, antihypertensive agents, hormone preparations and nutritional supplements.

The water-insoluble drug is preferably at least one selected from the group consisting of rapamycin, paclitaxel, docetaxel and everolimus. The rapamycin, paclitaxel, docetaxel, and everolimus include their analogs and/or derivatives, provided that the analogs and/or derivatives have a drug effect equivalent to the original. For instance, paclitaxel and docetaxel are in an analogous relationship, whereas rapamycin and everolimus are in a derivative relationship. Among these, more preferred is paclitaxel.

The coating composition contains the water-insoluble drug preferably in a concentration of 5 to 60 mg/mL, more preferably 20 to 50 mg/mL, and further preferably 30 to 40 mg/mL.

(2) Ester compounds of amino acids, which have a hydropathy index of the amino acid of zero or less than zero, and salts thereof.

2-1) Hydropathy Index of the Amino Acid

The hydropathy index of the amino acid represents the hydrophobicity or hydrophilicity of the amino acid. The higher the numerical value of the hydropathy index of the amino acid is, the more hydrophobic is the amino acid. Hereinafter, the hydropathy index of the amino acid may be referred to simply as "hydropathy index."

The hydropathy index is the hydropathy index according to "Kyte and Doolittle, J. Mol. Biol., 157, 105-132 (1982)."

The hydropathy index is not particularly limited, insofar as it is zero or less than zero.

Table 1 shows the hydropathy indexes of typical amino acids. In Table 1, "Amino acid" means amino acid, "CAS no." means CAS registry number, and "H.I." means hydropathy index.

TABLE 1

| Amino acid | CAS no. | H.I. |
| --- | --- | --- |
| Glycine | 56-40-6 | −0.4 |
| Asparagine | 70-47-3 | −3.5 |

TABLE 1-continued

| Amino acid | CAS no. | H.I. |
| --- | --- | --- |
| Serine | 56-45-1 | −0.8 |
| Aspartic acid | 56-84-8 | −3.5 |
| Glutamine | 56-85-9 | −3.5 |
| Glutamic acid | 56-86-0 | −3.5 |
| Threonine | 72-19-5 | −0.7 |
| Arginine | 74-79-3 | −4.5 |
| Histidine | 71-00-1 | −3.2 |
| Lysine | 56-87-1 | −3.9 |
| Tyrosine | 60-18-4 | −1.3 |
| Tryptophan | 73-22-3 | −0.9 |
| Cysteine | 52-90-4 | 2.5 |
| Methionine | 63-68-3 | 1.9 |
| Proline | 147-85-3 | −1.6 |
| Phenylalanine | 63-91-2 | 2.8 |
| Alanine | 56-41-7 | 1.8 |
| Valine | 72-18-4 | 4.2 |
| Leucine | 61-90-5 | 3.8 |
| Isoleucine | 73-32-5 | 4.5 |

2-2) Ester Compounds of Amino Acids, and Salts Thereof

The amino acids are not specifically restricted insofar as they have a hydropathy index of zero or less than zero; preferably, however, the amino acids are α-amino acids.

In addition, the ester compounds are not particularly restricted insofar as they are ester compounds of amino acids which have a hydropathy index of zero or less than zero. Preferably, however, the ester compounds are ester compounds of α-amino acids. More preferably, the ester compounds are ester compounds of at least one amino acid and a monohydric alcohol of up to five carbon atoms, the at least one amino acid being selected from the group consisting of glycine, serine, asparagine, aspartic acid, glutamine, glutamic acid, arginine, threonine, histidine, lysine, tyrosine, tryptophan, amino acids obtained by replacing at least one of hydrogen atoms of an amino group at α-position in the just-mentioned amino acids with an alkyl group of up to five carbon atoms, a benzyl group or a benzoyl group, proline, and amino acids obtained by replacing a hydrogen atom of an imino group of proline with an alkyl group of up to five carbon atoms, a benzyl group or a benzoyl group. Further preferably, the ester compounds are ester compounds represented by the following formula:

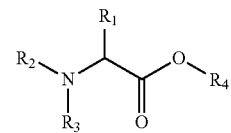

where $R_1$ is a hydrogen atom, guanidinopropyl group, carbamoylmethyl group, carboxymethyl group, methoxycarbonylmethyl group, ethoxycarbonylmethyl group, 2-carbamoylethyl group, 2-carboxyethyl group, 2-methoxycarbonylethyl group, 2-ethoxycarbonylethyl group, (1H-imidazol-4-yl)methyl group, 4-aminobutyl group, hydroxymethyl group, 1-hydroxyethyl group, (1H-indol-3-yl)methyl group or 4-hydroxybenzyl group, or forms a trimethylene group together with $R_2$, $R_2$ is a hydrogen atom or forms a trimethylene group together with $R_1$, $R_3$ is a hydrogen atom, an alkyl group of up to five carbon atoms, benzyl group or benzoyl group, and $R_4$ is an alkyl group of up to five carbon atoms. Still more preferably, the ester compound is at least one selected from the group consisting of benzylglycine ethyl ester, benzylglycine methyl ester, arginine ethyl ester, arginine methyl ester, benzoylarginine ethyl ester, benzoylarginine methyl ester, diethyl aspartate, methyl aspartate, dimethyl aspartate, glycine ethyl ester, glycine methyl ester, serine ethyl ester and serine methyl ester.

The salts of the ester compounds are not specifically restricted; however, the salts are preferably hydrochlorides or acetate, more preferably hydrochlorides. Besides, in the case where there is a free carboxyl group which is not part of an ester linkage, the salts of the ester compounds may be alkali metal salts, wherein the alkali metal is preferably sodium.

The salt of the ester compound of the amino acid is enhanced in polarity (water-solubility) by a salt of an amino group, for example, hydrochloride of an amino group. In addition, the salt of the ester compound of the amino acid can exhibit different properties such as hydrophilic property or hydrophobic property and basic property or acidic property, depending on the properties of a side chain or chains of the amino acid. The ester compounds of amino acids and the salts thereof are not specifically restricted, insofar as the amino acid has a hydropathy index of zero or less than zero. Preferably, however, they are polar. More preferably, they are polar and neutral, from the viewpoint of suppression of decomposition, such as hydrolysis, of themselves and/or the water-insoluble drug coexisting with them. Thus, the ester compounds of amino acids and the salts thereof can have polarity, according to the properties of their side chains and the polarity of the amino group. In addition, they have different kinds of polarity, depending on the kind of the side chain of the amino acid, and can give favorable coating compositions.

The coating composition contains the ester compound and/or the salts thereof in a total amount of preferably 5 to 200 parts by weight, more preferably 8 to 150 parts by weight, and further preferably 12 to 120 parts by weight, based on 100 parts by weight of the water-insoluble drug.

(3) Other Preferable Ingredients

Preferably, the coating composition further contains a lower alcohol. When the coating composition contains a lower alcohol, the water-insoluble drug's property for penetration into blood vessels can be enhanced, and uniformity of the drug coating layer can be enhanced. The lower alcohol is not specifically restricted, insofar as it is an alcohol of up to five carbon atoms. Preferably, the lower alcohol is a triol or tetraol of up to five carbon atoms. More preferably, the lower alcohol is glycerine (also referred to as "glycerol" or "propane-1,2,3-triol"), 1,2,4-butanetriol (also referred to as "butane-1,2,4-triol") or erythritol (also referred to as "(2R, 3S)-butane-1,2,3,4-tetraol"). Further preferably, the lower alcohol is glycerine.

In the case where the coating composition contains the lower alcohol, its content is not particularly limited. The lower alcohol content is preferably 10 to 500 parts by weight, more preferably 30 to 300 parts by weight, and further preferably 50 to 200 parts by weight, based on 100 parts by weight of the water-insoluble drug.

(4) Other Ingredients

In addition to the aforementioned ingredients, the coating composition may contain solvent for these ingredients, such as water, ethanol, acetone, tetrahydrofuran, etc. Furthermore, the coating composition may contain other additives on condition that the additives are not detrimental to the effect that can be obtained.

2. Drug Coating Layer

The drug coating layer is a layer formed on at least part of a surface of a medical device by use of the coating composition. The drug coating layer is a layer which contains the water-insoluble drug and at least one selected from the group consisting of the ester compounds of amino acids, which have a hydropathy index of the amino acid of zero or less than zero, and the salts thereof.

The drug coating layer can be formed by coating a surface of a medical device with the coating composition, followed by drying. This method, however, is not restrictive.

The amount of the drug contained in the drug coating layer is not particularly limited. The drug is preferably contained in the drug coating layer in a density of 0.1 to 10 $\mu g/mm^2$, more preferably 0.5 to 5 $\mu g/mm^2$, further preferably 0.5 to 3.5 $\mu g/mm^2$, and further preferably 1.0 to 3.0 $\mu g/mm^2$.

3. Drug-Eluting Medical Device

The drug-eluting medical device has the drug coating layer, either directly on a surface thereof or on a surface thereof having been pretreated with an organic solvent, primer irradiation, irradiation with UV rays, or the like. The medical device is preferably a medical device which is radially (circumferentially) expandable in a lumen such as a blood vessel, more preferably a balloon catheter or a stent.

On at least part of a surface of the drug-eluting medical device is formed the drug coating layer which contains the water-insoluble drug and at least one selected from the group consisting of the ester compounds of amino acids, which have a hydropathy index of the amino acid of zero or less than zero, and the salts thereof. The drug coating layer has a high affinity for the surface of the medical device, so that it is not susceptible to peeling or separation from the medical device surface during the process of delivery of the medical device. Furthermore, the drug coating layer has a high affinity for the tissue of an affected part of lesion, so that the drug is expected to be rapidly eluted at the target tissue. In the case of a balloon catheter, the drug coating layer is formed on at least part of an outer surface of an expandable portion (balloon). Besides, in the case of a stent, the drug coating layer is formed on at least part of an outer surface of an expandable portion.

The material of the expandable portion of the medical device is preferably a material which has a certain degree of flexibility and has a certain degree of rigidity such that upon arrival at a blood vessel, tissue or the like the expandable portion is expanded so that the drug can be released from the drug coating layer present on the surface of the expandable portion. Specifically, the surface of the expandable portion on which the drug coating layer is provided is formed of a resin. The resin constituting the surface of the expandable portion is not specifically restricted, and preferable examples of the material include polyamides. In other words, at least part of the surface of the expandable portion of the medical device to be coated with the drug is made of a polyamide. The polyamide is not specifically restricted insofar as it is a polymer having an amide linkage. Examples of the polyamide include aromatic polyamides, for example, homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylenediammonium adipate copolymer (nylon 6/66), etc., copolymer of adipic acid with metaxylenediamine, and copolymers of hexamethylenediamine with m,p-phthalic acids, etc. Furthermore, polyamide elastomers which are block copolymers having nylon 6, nylon 66, nylon 11, nylon 12 or the like as a hard segment and having a polyalkylene glycol, a polyether, an aliphatic polyester or the like as a soft segment can also be used as a base material for the medical device. The polyamides may be used either singly or in combination of two or more of them.

In addition, for other portions than the expandable portion of the medical device, there can be used thermoplastic resins, for example, polyolefins such as polyethylene, polypropylene, ethylene-propylene copolymer, etc., polyesters such as polyethylene terephthalate, etc., polyvinyl chloride, ethylene-vinyl acetate copolymer, crosslinked ethylene-vinyl acetate copolymer, polyurethane, etc., polyamides, polyamide elastomers, silicone rubbers, latex rubbers, and so on.

4. Method of Treatment in which Drug-Eluting Medical Device is Used

A method of treatment in which the drug-eluting medical device is used includes a step of eluting the drug from the drug coating layer formed on at least part of the surface of the medical device. To be more specific, the method of treatment in which the drug-eluting medical device is used preferably includes: a step of delivering the medical device into a lumen; a step of radially expanding the medical device inside the lumen; and a step of eluting the drug from the drug coating layer formed on at least part of the surface of the medical device, thereby allowing the drug to act on the lumen.

The step of delivering the drug-eluting medical device into the lumen can be carried out in the same manner as in the cases of conventionally known balloons and stents. For instance, in the case where the drug-eluting balloon or stent is to be delivered to a stenosed part of a coronary artery, a tube-shaped guiding catheter is inserted via a patient's carpal or femoral artery to an inlet portion of a cardiac coronary artery, a guide wire is inserted into the guiding catheter, and the balloon catheter is inserted along the guide wire, whereby the balloon or stent can be delivered to the stenosed part.

The step of radially expanding the drug-eluting medical device in the lumen can be carried out in the same manner as in the cases of conventionally known balloons and stents.

The step of eluting the drug from the drug coating layer formed on at least part of the surface of the drug-eluting medical device to permit the drug to act on the lumen can be carried out by a method in which the medical device is expanded inside the lumen and is held for a time of several tens of seconds to several minutes while keeping the drug-eluting balloon expanded or in which the drug-eluting stent is placed indwelling in the lumen. This ensures that the lumen is expanded and the drug of the drug coating layer acts on the tissue of the lumen.

The method of treatment in which the drug-eluting medical device is used can be applied, for example, to treatment of angiostenosis. According to the method of treatment, it is possible to prevent restenosis, by utilizing a cell proliferation-suppressing agent such as carcinostatic (e.g., paclitaxel) or immunosuppressant as the drug.

The ester compounds of amino acids, which have a hydropathy index of the amino acid of zero or less than zero, and the salts thereof to be contained in the coating composition are highly biocompatible (for example, they do not induce thrombus formation) and are rapidly biodegradable. Therefore, it is possible to provide a drug-eluting medical device which is favorable from the viewpoint of safety.

EXAMPLES

Now, various illustrative embodiments will be described more in detail below, by showing examples. It is to be noted, however, that the above-described aspects are not restricted to the following examples.

[Fabrication of Drug-Eluting Balloon or Preparation of Commercialized Balloon]

<Preparation Examples of Amino Acid Ester Solution>

(30 mg/mL Arginine Ethyl Ester Solution)

L-Arginine ethyl ester dihydrochloride (CAS No. 36589-29-4) in an amount of 60 mg was weighed, and was added to and dissolved in an ethanol-water mixture containing 1 mL of anhydrous ethanol and 1 mL of reverse osmosis (RO) water, to prepare a 30 mg/mL L-arginine ethyl ester solution.

(30 mg/mL Nα-Benzoyl-L-Arginine Ethyl Ester Solution)

Nα-Benzoyl-L-arginine ethyl ester hydrochloride (CAS No. 2645-08-1) in an amount of 60 mg was weighed, and was added to and dissolved in an ethanol-water mixture containing 1 mL of anhydrous ethanol and 1 mL of RO water, to prepare a 30 mg/mL Nα-benzoyl-L-arginine ethyl ester solution.

(30 mg/mL Dimethyl L-Aspartate Solution)

Dimethyl L-aspartate hydrochloride (CAS No. 32213-95-9) in an amount of 60 mg was weighed, and was added to and dissolved in an ethanol-water mixture containing 1 mL of anhydrous ethanol and 1 mL of RO water, to prepare a 30 mg/mL dimethyl L-aspartate solution.

(50 mg/mL Dimethyl L-Aspartate Solution)

Dimethyl L-aspartate hydrochloride in an amount of 50 mg was weighed, and was added to and dissolved in an ethanol-water mixture containing 0.5 mL of anhydrous ethanol and 0.5 mL of RO water, to prepare a 50 mg/mL dimethyl L-aspartate solution.

(30 mg/mL L-Serine Ethyl Ester Solution)

L-Serine ethyl ester hydrochloride (CAS No. 26348-61-8) in an amount of 60 mg was weighed, and was added to and dissolved in an ethanol-water mixture containing 1 mL of anhydrous ethanol and 1 mL of RO water, to prepare a 30 mg/mL L-serine ethyl ester solution.

(70 mg/mL L-Serine Ethyl Ester Solution 1)

L-Serine ethyl ester hydrochloride in an amount of 140 mg was weighed, and was added to and dissolved in an ethanol-water mixture containing 1 mL of anhydrous ethanol and 1 mL of RO water, to prepare a 70 mg/mL L-serine ethyl ester solution.

(70 mg/mL L-Serine Ethyl Ester Solution 2)

L-Serine ethyl ester hydrochloride in an amount of 140 mg was weighed, and was added to and dissolved in an ethanol-water mixture containing 1.5 mL of RO water and 0.5 mL of anhydrous ethanol, to prepare a 70 mg/mL L-serine ethyl ester solution.

(70 mg/mL L-Serine Ethyl Ester Solution 3)

L-Serine ethyl ester hydrochloride in an amount of 140 mg was weighed, and was added to and dissolved in 2 mL of RO water, to prepare a 70 mg/mL L-serine ethyl ester solution.

(30 mg/mL Glycine Ethyl Ester Solution)

Glycine ethyl ester hydrochloride (CAS No. 623-33-6) in an amount of 60 mg was weighed, and was added to and dissolved in an ethanol-water mixture containing 1 mL of anhydrous ethanol and 1 mL of RO water, to prepare a 30 mg/mL glycine ethyl ester solution.

(40 mg/mL N-Benzylglycine Ethyl Ester Solution)

N-Benzylglycine ethyl ester hydrochloride (CAS No. 6344-42-9) in an amount of 80 mg was weighed, and was added to and dissolved in an ethanol-water mixture containing 1 mL of anhydrous ethanol and 1 mL of RO water, to prepare a 40 mg/mL N-benzylglycine ethyl ester solution.
(40 mg/mL L-Alanine Ethyl Ester Solution)

L-Alanine ethyl ester hydrochloride (CAS No. 1115-59-9) in an amount of 80 mg was weighed, and was added to and dissolved in an ethanol-water mixture containing 1 mL of anhydrous ethanol and 1 mL of RO water, to prepare a 40 mg/mL L-alanine ethyl ester solution.
(30 mg/mL L-Valine Methyl Ester Solution)

L-Valine methyl ester hydrochloride (CAS No. 6306-52-1) in an amount of 54 mg was weighed, and was added to and dissolved in an ethanol-water mixture containing 1.5 mL of anhydrous ethanol and 0.3 mL of RO water, to prepare a 30 mg/mL L-valine methyl ester solution.
(50 mg/mL L-Valine Methyl Ester Solution)

L-Valine methyl ester hydrochloride (CAS No. 6306-52-1) in an amount of 90 mg was weighed, and was added to and dissolved in an ethanol-water mixture containing 1.5 mL of anhydrous ethanol and 0.3 mL of RO water, to prepare a 50 mg/mL L-valine methyl ester solution.
<Preparation Examples of Amino Acid Solution>
(40 mg/mL L-Arginine Solution)

L-Arginine hydrochloride (CAS No. 1119-34-2) in an amount of 80 mg was weighed, and was added to and dissolved in an ethanol-water mixture containing 1 mL of anhydrous ethanol and 1 mL of RO water, to prepare a 40 mg/mL L-arginine solution.
(70 mg/mL L-Serine Solution)

L-Serine (CAS No. 56-45-1) in an amount of 70 mg was weighed, and was added to and dissolved in 1 mL of RO water, to prepare a 70 mg/mL L-serine solution.
<Preparation Examples of Paclitaxel Solution>
(20 mg/mL Paclitaxel Solution)

Paclitaxel (CAS No. 33069-62-4) in an amount of 40 mg was weighed, and was added to and dissolved in an ethanol-acetone mixture containing 1 mL of anhydrous ethanol and 1 mL of acetone, to prepare a 20 mg/mL paclitaxel solution.
(40 mg/mL Paclitaxel Solution 1)

Paclitaxel (CAS No. 33069-62-4) in an amount of 80 mg was weighed, and was added to and dissolved in an ethanol-acetone mixture containing 1 mL of anhydrous ethanol and 1 mL of acetone, to prepare a 40 mg/mL paclitaxel solution 1.
(40 mg/mL Paclitaxel Solution 2)

Paclitaxel in an amount of 160 mg was weighed, and was added to and dissolved in 4 mL of tetrahydrofuran (CAS No. 109-99-9), to prepare a 40 mg/mL paclitaxel solution 2.
(56 mg/mL Paclitaxel Solution 1)

Paclitaxel in an amount of 336 mg was weighed, and was added to and dissolved in 6 mL of tetrahydrofuran, to prepare a 56 mg/mL paclitaxel solution 1.
(56 mg/mL Paclitaxel Solution 2)

Paclitaxel in an amount of 224 mg was weighed, and was added to and dissolved in a THF-ethanol mixture containing 2.66 mL of tetrahydrofuran and 1.34 mL of anhydrous ethanol, to prepare a 56 mg/mL paclitaxel solution 2.
(56 mg/mL Paclitaxel Solution 3)

Paclitaxel in an amount of 336 mg was weighed, and was added to and dissolved in a THF-ethanol mixture containing 4 mL of tetrahydrofuran and 2 mL of anhydrous ethanol, to prepare a 56 mg/mL paclitaxel solution 3.
(56 mg/mL Paclitaxel Solution 4)

Paclitaxel in an amount of 224 mg was weighed, and was added to and dissolved in a THF-ethanol mixture containing 2 mL of tetrahydrofuran and 2 mL of anhydrous ethanol, to prepare a 56 mg/mL paclitaxel solution 4.
(56 mg/mL Paclitaxel Solution 5)

Paclitaxel in an amount of 448 mg was weighed, and was added to and dissolved in an ethanol-acetone mixture containing 4 mL of anhydrous ethanol and 4 mL of acetone, to prepare a 56 mg/mL paclitaxel solution 5.
<Preparation Examples of Glycerine Solution>
(50% Glycerine Solution 1)

Glycerine (CAS No. 56-81-5) in an amount of 100 μL and anhydrous ethanol in an amount of 100 μL were mixed together, to prepare a 50% glycerine solution 1.
(50% Glycerine Solution 2)

Glycerine in an amount of 500 μL and anhydrous ethanol in an amount of 500 μL were mixed together, to prepare a 50% glycerine solution 2.

Example 1

(1) Preparation of Coating Solution 1

The 40 mg/mL N-benzylglycine ethyl ester solution in an amount of 25 μL was mixed with 150 μL of the 40 mg/mL paclitaxel solution 1 and 25 μL of anhydrous ethanol, to prepare a coating solution 1. The mass ratio of benzylglycine ethyl ester to paclitaxel in the coating solution 1 (BnGly-OEt/PTX) was 0.50.

(2) Coating of Balloon with Drug

A balloon catheter (produced by Terumo Corporation, the material of a balloon (expandable portion) is nylon elastomer), whose expandable portion is 3.0 mm in diameter and 20 mm in length when expanded, was prepared. The balloon in its expanded state was coated with the coating solution 1 so that the amount of paclitaxel would be about 2 μg/mm$^2$, by use of a pipette, followed by drying, to fabricate a drug-eluting balloon.

Example 2

(1) Preparation of Coating Solution 2

The 30 mg/mL L-arginine ethyl ester solution in an amount of 50 μL was mixed with 60 μL of the 40 mg/mL paclitaxel solution 1, to prepare a coating solution 2. The mass ratio of arginine ethyl ester to paclitaxel in the coating solution 2 (Arg-OEt/PTX) was 0.63.

(2) Coating of Balloon with Drug

A drug-eluting balloon was fabricated in the same manner as in Example 1, except that the coating solution 2 was used in place of the coating solution 1.

Example 3

(1) Preparation of Coating Solution 3

The 30 mg/mL Nα-benzoyl-L-arginine ethyl ester solution in an amount of 50 μL was mixed with 50 μL of the 40 mg/mL paclitaxel solution 1, to prepare a coating solution 3. The mass ratio of Nα-benzoyl-L-arginine ethyl ester to paclitaxel in the coating solution 3 (BzArg-OEt/PTX) was 0.75.

(2) Coating of Balloon with Drug

A drug-eluting balloon was fabricated in the same manner as in Example 1, except that the coating solution 3 was used in place of the coating solution 1.

Example 4

(1) Preparation of Coating Solution 4

The 30 mg/mL dimethyl L-aspartate solution in an amount of 50 μL was mixed with 75 μL of the 40 mg/mL paclitaxel solution 1, to prepare a coating solution 4. The mass ratio of dimethyl L-aspartate to paclitaxel in the coating solution 4 (Asp-DiOMe/PTX) was 0.63.

(2) Coating of Balloon with Drug

A drug-eluting balloon was fabricated in the same manner as in Example 1, except that the coating solution 4 was used in place of the coating solution 1.

Example 5

(1) Preparation of Coating Solution 5

The 30 mg/mL glycine ethyl ester solution in an amount of 50 μL was mixed with 110 μL of the 40 mg/mL paclitaxel solution 1, to prepare a coating solution 5. The mass ratio of glycine ethyl ester to paclitaxel in the coating solution 5 (Gly-OEt/PTX) was 0.63.

(2) Coating of Balloon with Drug

A drug-eluting balloon was fabricated in the same manner as in Example 1, except that the coating solution 5 was used in place of the coating solution 1.

Example 6

(1) Preparation of Coating Solution 6

The 30 mg/mL L-serine ethyl ester solution in an amount of 50 μL was mixed with 90 μL of the 40 mg/mL paclitaxel solution 1, to prepare a coating solution 6. The mass ratio of L-serine ethyl ester to paclitaxel in the coating solution 6 (Ser-OEt/PTX) was 0.42.

(2) Coating of Balloon with Drug

A drug-eluting balloon was fabricated in the same manner as in Example 1, except that the coating solution 6 was used in place of the coating solution 1.

Example 7

(1) Preparation of Coating Solution 7

The 30 mg/mL L-arginine ethyl ester solution in an amount of 160 μL was mixed with 200 μL of the 40 mg/mL paclitaxel solution 1 and 20 μL of the 50% glycerine solution 1, to prepare a coating solution 7. The mass ratio of L-arginine ethyl ester to paclitaxel in the coating solution 7 (Arg-OEt/PTX) was 0.60.

The coating solution 7 is a coating solution which contains glycerine, further, in addition to the L-arginine ethyl ester (Arg-OEt; having a hydropathy index of the amino acid of −4.5) and paclitaxel (PTX).

(2) Coating of Balloon with Drug

A drug-eluting balloon was fabricated in the same manner as in Example 1, except that the coating solution 7 was used in place of the coating solution 1.

Example 8

(1) Preparation of Coating Solution 8

The 50 mg/mL dimethyl L-aspartate solution in an amount of 90 μL was mixed with 240 μL of the 40 mg/mL paclitaxel solution 2, to prepare a coating solution 8. The mass ratio of dimethyl L-aspartate to paclitaxel in the coating solution 8 (Asp-DiOMe/PTX) was 0.47.

(2) Coating of Balloon with Drug

A drug-eluting balloon was fabricated in the same manner as in Example 1, except that the coating solution 8 was used in place of the coating solution 1 and that the coating was so conducted that the amount of paclitaxel would be about 3 μg/mm².

Example 9

(1) Preparation of Coating Solution 9

The 70 mg/mL L-serine ethyl ester solution 1 in an amount of 80 μL was mixed with 240 μL of the 56 mg/mL paclitaxel solution 1 and 16 μL of the 50% glycerine solution 2, to prepare a coating solution 9. The mass ratio of L-serine ethyl ester to paclitaxel in the coating solution 9 (Ser-OEt/PTX) was 0.42.

(2) Coating of Balloon with Drug

A drug-eluting balloon was fabricated in the same manner as in Example 1, except that the coating solution 9 was used in place of the coating solution 1 and that the coating was so conducted that the amount of paclitaxel would be about 3 μg/mm².

Example 10

(1) Preparation of Coating Solution 10

The 70 mg/mL L-serine ethyl ester solution 1 in an amount of 80 μL was mixed with 240 μL of the 56 mg/mL paclitaxel solution 1, to prepare a coating solution 10. The mass ratio of L-serine ethyl ester to paclitaxel in the coating solution 10 (Ser-OEt/PTX) was 0.42.

(2) Coating of Balloon with Drug

A drug-eluting balloon was fabricated in the same manner as in Example 1, except that the coating solution 10 was used in place of the coating solution 1 and that the coating was so performed that the amount of paclitaxel would be about 3 μg/mm².

Example 11

(1) Preparation of Coating Solution 11

The 70 mg/mL L-serine ethyl ester solution 1 in an amount of 800 μL was mixed with 2400 μL of the 56 mg/mL paclitaxel solution 2, to prepare a coating solution 11. The mass ratio of L-serine ethyl ester to paclitaxel in the coating solution 11 (Ser-OEt/PTX) was 0.42.

(2) Coating of Balloon with Drug

A drug-eluting balloon was fabricated in the same manner as in Example 1, except that the coating solution 11 was used in place of the coating solution 1 and that the coating was so conducted that the amount of paclitaxel would be about 3 μg/mm².

Example 12

(1) Preparation of Coating Solution 12

The 70 mg/mL L-serine ethyl ester solution 1 in an amount of 600 μL was mixed with 1800 μL of the 56 mg/mL paclitaxel solution 5, to prepare a coating solution 12. The mass ratio of L-serine ethyl ester to paclitaxel in the coating solution 12 (Ser-OEt/PTX) was 0.42.

(2) Coating of Balloon with Drug

A drug-eluting balloon was fabricated in the same manner as in Example 1, except that the coating solution 12 was used in place of the coating solution 1 and that the coating was so performed that the amount of paclitaxel would be about 3 μg/mm².

Example 13

(1) Preparation of Coating Solution 13

The 70 mg/mL L-serine ethyl ester solution 1 in an amount of 600 μL was mixed with 1800 μL of the 56 mg/mL paclitaxel solution 3, to prepare a coating solution 13. The mass ratio of L-serine ethyl ester to paclitaxel in the coating solution 13 (Ser-OEt/PTX) was 0.42.

(2) Coating of Balloon with Drug

A drug-eluting balloon was fabricated in the same manner as in Example 1, except that the coating solution 13 was used in place of the coating solution 1 and that the coating was carried out so that the amount of paclitaxel would be about 3 μg/mm$^2$.

Example 14

(1) Preparation of Coating Solution 14

The 70 mg/mL L-serine ethyl ester solution 2 in an amount of 500 μL was mixed with 1500 μL of the 56 mg/mL paclitaxel solution 4, to prepare a coating solution 14. The mass ratio of L-serine ethyl ester to paclitaxel in the coating solution 14 (Ser-OEt/PTX) was 0.42.

(2) Coating of Balloon with Drug

A drug-eluting balloon was fabricated in the same manner as in Example 1, except that the coating solution 14 was used in place of the coating solution 1 and that the coating was so conducted that the amount of paclitaxel would be about 3 μg/mm$^2$.

Example 15

(1) Preparation of Coating Solution 15

The 70 mg/mL L-serine ethyl ester solution 3 in an amount of 500 μL was mixed with 1500 μL of the 56 mg/mL paclitaxel solution 4, to prepare a coating solution 15. The mass ratio of L-serine ethyl ester to paclitaxel in the coating solution 15 (Ser-OEt/PTX) was 0.42.

(2) Coating of Balloon with Drug

A drug-eluting balloon was fabricated in the same manner as in Example 1, except that the coating solution 15 was used in place of the coating solution 1 and that the coating was so performed that the amount of paclitaxel would be about 3 μg/mm$^2$.

Comparative Example C1

(1) Preparation of Paclitaxel Solution 16

The 40 mg/mL L-alanine ethyl ester solution in an amount of 60 μL was mixed with 50 μL of the 40 mg/mL paclitaxel solution 1, to prepare a paclitaxel solution 16. The mass ratio of L-alanine ethyl ester to paclitaxel in the paclitaxel solution 16 (Ala-OEt/PTX) was 1.20.

(2) Coating of Balloon with Drug

A drug-eluting balloon was fabricated in the same manner as in Example 1, except that the paclitaxel solution 16 was used in place of the coating solution 1.

Comparative Example C2

(1) Preparation of Paclitaxel Solution 17

The 30 mg/mL L-valine methyl ester solution in an amount of 70 μL was mixed with 50 μL of the 40 mg/mL paclitaxel solution 1, to prepare a paclitaxel solution 17. The mass ratio of L-valine methyl ester to paclitaxel in the paclitaxel solution 17 (Val-OMe/PTX) was 1.05.

(2) Coating of Balloon with Drug

A drug-eluting balloon was fabricated in the same manner as in Example 1, except that the paclitaxel solution 17 was used in place of the coating solution 1.

Comparative Example C3

(1) Preparation of Paclitaxel Solution 18

The 40 mg/mL arginine solution in an amount of 60 μL was mixed with 50 μL of the 40 mg/mL paclitaxel solution 1, to prepare a paclitaxel solution 18. The mass ratio of L-arginine to paclitaxel in the paclitaxel solution 18 (Arg/PTX) was 1.05.

(2) Coating of Balloon with Drug

A drug-eluting balloon was fabricated in the same manner as in Example 1, except that the paclitaxel solution 18 was used in place of the coating solution 1.

Comparative Example C4

(1) Preparation of Paclitaxel Solution 19

The 20 mg/mL paclitaxel solution was made to be a paclitaxel solution 19.

The paclitaxel solution 19 is a paclitaxel (PTX) solution which does not contain an amino acid ester or an amino acid.

(2) Coating of Balloon with Drug

A drug-eluting balloon was fabricated in the same manner as in Example 1, except that the paclitaxel solution 19 was used in place of the coating solution 1 and that the coating was so conducted that the amount of paclitaxel would be about 3 μg/mm$^2$.

Comparative Example C5

(1) Preparation of Paclitaxel Solution 20

The 50 mg/mL L-valine methyl ester solution in an amount of 80 μL was mixed with 240 μL of the 40 mg/mL paclitaxel solution 2, to prepare a paclitaxel solution 20. The mass ratio of L-valine methyl ester to paclitaxel in the paclitaxel solution 20 (Val-OMe/PTX) was 0.42.

(2) Coating of Balloon with Drug

A drug-eluting balloon was fabricated in the same manner as in Example 1, using the paclitaxel solution 20 prepared above.

Comparative Example C6

A commercialized balloon catheter IN.PACT (produced by Invatec) was prepared. The balloon in Comparative Example C6 is a drug-eluting balloon with a surface coated with paclitaxel.

Comparative Example C7

A balloon catheter (produced by Terumo C; formed from nylon elastomer), whose expandable portion is 3.0 mm in diameter and 20 mm in length when expanded, was prepared. The balloon in Comparative Example C7 is a non-drug-coated balloon that is not coated with a drug.

Comparative Example C8

(1) Preparation of Coating Solution 21

The 70 mg/mL L-serine solution in an amount of 300 μL was mixed with 900 μL of the 56 mg/mL paclitaxel solution 3, to prepare a coating solution 21. The coating solution appeared cloudy.

(2) Coating of Balloon with Drug

Since the coating solution 21 was cloudy, the balloon could not be coated therewith. Accordingly, it has been verified that a drug coating solution cannot be prepared using the L-serine solution.

The coating solution prepared, the drug and the amino acid ester hydrochloride or amino acid contained in the coating solution, the hydropathy index of the amino acid ester hydrochloride or amino acid, the lower alcohol (only in the cases where a lower alcohol was used) and the solvents, for Examples 1 to 15 and Comparative Examples C1 to C5 and C8 are set forth in Table 2. In Table 2, 1 to 15 in the column of "Example/Comparative example" are Examples, whereas C1 to C5 and C8 are Comparative examples. The "PTX" in the column of "Drug" means paclitaxel. In the column of "Amino acid ester/amino acid," "Bn-Gly-Et" means N-benzylglycine ethyl ester, "L-Arg-Et" means L-arginine ethyl ester, "Bnz-Arg-Et" means Nα-benzoyl-L-arginine ethyl ester, "L-Asp-2Me" means dimethyl L-aspartate, "Gly-Et" means glycine ethyl ester, "L-Ser-Et" means L-serine ethyl ester, "L-Ala-Et" means L-alanine ethyl ester, "L-Val-Me" means L-valine methyl ester, "L-Arg" means L-arginine, and "L-Ser" means L-serine, respectively. The "Glycerine" in the column of "Lower alcohol" means glycerine. In the column of "Solvents," "EtOH" means ethanol, "RO-W" means RO water, "THF" means tetrahydrofuran, and "AC" means acetone, respectively.

TABLE 2

| Examples/ Comparative examples | No. | Drug | Amino acid ester/amino acid Abbreviation | Hydrophobicity Index | Lower alcohol | Solvents |
|---|---|---|---|---|---|---|
| 1 | 1 | PTX | Bn-Gly-Et | −0.4 | — | EtOH/RO-W |
| 2 | 2 | PTX | L-Arg-Et | −4.5 | — | EtOH/RO-W |
| 3 | 3 | PTX | Bnz-L-Arg-Et | −4.5 | — | EtOH/RO-W |
| 4 | 4 | PTX | L-Asp-2Me | −3.5 | — | EtOH/RO-W |
| 5 | 5 | PTX | Gly-Et | −0.4 | — | EtOH/RO-W |
| 6 | 6 | PTX | L-Ser-Et | −0.8 | — | EtOH/RO-W |
| 7 | 7 | PTX | L-Arg-Et | −4.5 | Glycerine | EtOH/RO-W |
| 8 | 8 | PTX | L-Asp-2Me | −3.5 | — | EtOH/RO-W |
| 9 | 9 | PTX | L-Ser-Et | −0.8 | Glycerine | THF/EtOH/RO-W |
| 10 | 10 | PTX | L-Ser-Et | −0.8 | — | THF/EtOH/RO-W |
| 11 | 11 | PTX | L-Ser-Et | −0.8 | — | THF/EtOH/RO-W |
| 12 | 12 | PTX | L-Ser-Et | −0.8 | — | THF/AC/RO-W |
| 13 | 13 | PTX | L-Ser-Et | −0.8 | — | THF/EtOH/RO-W |
| 14 | 14 | PTX | L-Ser-Et | −0.8 | — | THF/EtOH/RO-W |
| 15 | 15 | PTX | L-Ser-Et | −0.8 | — | THF/EtOH/RO-W |
| C1 | 16 | PTX | L-Ala-Et | 1.8 | — | EtOH/RO-W |
| C2 | 17 | PTX | L-Val-Me | 4.2 | — | EtOH/RO-W |
| C3 | 18 | PTX | L-Arg | −4.5 | — | EtOH/RO-W |
| C4 | 19 | PTX | — | — | — | EtOH/RO-W |
| C5 | 20 | PTX | L-Val-Me | 4.2 | — | EtOH/RO-W |
| C8 | 21 | PTX | L-Ser | −0.8 | — | THF/EtOH/RO-W |

Measurement of Amount of Paclitaxel in Coating on Balloon

For the drug-eluting balloons in Examples 1 to 15 and Comparative examples C1 to C5, the amount of paclitaxel in the coating on the balloon was measured by the following procedure.

1. Method

The drug-eluting balloon prepared was immersed in a methanol solution, followed by shaking by use of a shaking machine for 10 minutes, whereby paclitaxel in the coating on the balloon was extracted. The absorptivity of the methanol solution into which paclitaxel had been extracted was measured by high performance liquid chromatography using an ultraviolet-visible absorptiometer, and the amount of paclitaxel per balloon ([μg/balloon]) was determined. Furthermore, from the thus determined amount of paclitaxel and the balloon surface area, the amount of paclitaxel per unit area ([μg/mm$^2$]) was calculated.

2. Results

The results as set forth in Table 3 were obtained. In Table 3, 1 to 15 in the column of "Examples/Comparative examples" are Examples, and C1 to C5 in the column are Comparative Examples. Besides, in Table 3, "Surface area of a balloon" represents the surface area of the balloon in an expanded state (unit: mm$^2$), "per each" under "Amount of PTX on a balloon" represents the amount of paclitaxel per each balloon (unit: μg/balloon), and "per unit area" under "Amount of PTX on a balloon" represents the amount of paclitaxel per 1 mm$^2$ of surface area of the balloon (unit: μg/mm$^2$), respectively.

TABLE 3

| Examples/ Comparative examples | Coating solution No. | Surface area of a balloon [mm$^2$] | Amount of PTX on a balloon | |
|---|---|---|---|---|
| | | | per each [μg/balloon] | per unit area [μg/mm$^2$] |
| 1 | 1 | 188.4 | 305.8 | 1.6 |
| 2 | 2 | 188.4 | 278.3 | 1.5 |
| 3 | 3 | 188.4 | 290.4 | 1.5 |
| 4 | 4 | 188.4 | 342.5 | 1.8 |
| 5 | 5 | 188.4 | 294.3 | 1.6 |
| 6 | 6 | 188.4 | 285.4 | 1.5 |
| 7 | 7 | 188.4 | 333.1 | 1.8 |
| 8 | 8 | 188.4 | 597.2 | 3.2 |
| 9 | 9 | 188.4 | 504.5 | 2.7 |
| 10 | 10 | 188.4 | 560.2 | 3.0 |
| 11 | 11 | 188.4 | 588.9 | 3.1 |
| 12 | 12 | 188.4 | 489.2 | 2.6 |
| 13 | 13 | 188.4 | 523.0 | 2.8 |
| 14 | 14 | 188.4 | 653.2 | 3.5 |
| 15 | 15 | 188.4 | 652.6 | 3.5 |

TABLE 3-continued

| Examples/ Comparative examples | Coating solution No. | Surface area of a balloon [mm²] | Amount of PTX on a balloon per each [µg/balloon] | Amount of PTX on a balloon per unit area [µg/mm²] |
|---|---|---|---|---|
| C1 | 16 | 188.4 | 321.7 | 1.7 |
| C2 | 17 | 188.4 | 367.0 | 2.0 |
| C3 | 18 | 188.4 | 342.5 | 1.8 |
| C4 | 19 | 188.4 | 492.4 | 2.6 |
| C5 | 20 | 188.4 | 579.5 | 3.1 |

As shown in Table 3, in every one of Examples 1 to 15 and Comparative Examples C1 to C5, the amount of paclitaxel in the coating on the balloon was about 2 µg/mm² (Examples 1 to 7, Comparative Examples C1 to C3) or about 3 µg/mm² (Examples 8 to 15, Comparative Examples C4 and C5), which means that an intended amount of paclitaxel could be provided in the coating on the balloon surface.

Evaluation of Drug Coating Layer Durability by Use of Imitative Blood Vessel

In order to evaluate how much the drug coating layer is separated from the balloon in the process of delivery of the balloon to an affected part of a lesion, for the drug-eluting balloons in Examples 1 to 7 and Comparative Examples C1 to C4, a drug coating layer durability test was carried out by performing a delivery operation using an imitative blood vessel and determining the amount of paclitaxel remaining on the balloon after the delivery.

1. Method (1) A hollow imitative blood vessel 1 with a 90-degree angle was prepared, and a guiding catheter 2 (outside diameter: 5 Fr.) was inserted and passed in the imitative blood vessel 1 (see FIG. 1).

(2) The inside of the guiding catheter 2 was filled with phosphate buffered saline (PBS) warmed up to 37° C.

(3) The drug-eluting balloon fabricated (sized 3.0 mm in diameter and 20 mm in length when expanded) was folded by use of a wrapping machine.

(4) The balloon catheter 3 after the wrapping was inserted into the guiding catheter filled with the PBS, and a delivery operation of delivering the balloon 4 toward an outlet of the guiding catheter was performed for one minute.

(5) The balloon having been delivered in the guiding catheter was recovered, and the amount of paclitaxel remaining on the balloon (amount of PTX remaining) was determined by liquid chromatography. Furthermore, from the amount of paclitaxel in the coating on the drug-eluting balloon (amount of PTX coated on a balloon) and the amount of PTX remaining, the remaining rate of paclitaxel on the balloon (rates of PTX remaining) was calculated.

2. Results

The results as set forth in Table 4 were obtained. In Table 4, 1 to 7 in the column of "Examples/Comparative examples" are Examples, and C1 to C4 in the column are Comparative Examples. Besides, in Table 4, "Amount of PTX coated on a balloon" represents the amount of paclitaxel provided in the coating per each drug-eluting balloon (unit: µg/balloon), "Amount of PTX remaining on a balloon" represents the amount of paclitaxel remaining per each balloon after the delivery operation (unit: µg/balloon), and "Rates of PTX remaining on a balloon" represents the rates of paclitaxel remaining on the balloon after the delivery operation (unit: mass %).

Figure 2:
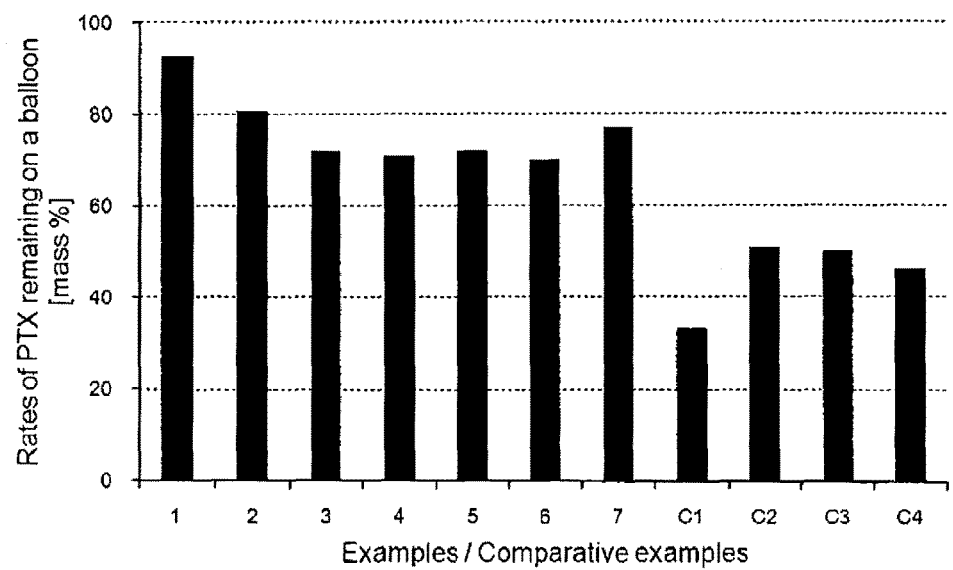
FIG. 2 is a graph representing the rate of paclitaxel remaining on the balloon after a delivery operation of drug-eluting balloons in Examples 1 to 7 and Comparative Examples C1 to C4, in an evaluation of the durability of a drug coating layer using the imitative blood vessel.

In addition, FIG. 2 shows a graph representing rates of paclitaxel remaining on the balloon after the delivery operation of the drug-eluting balloon in Examples 1 to 7 and Comparative Examples C1 to C4, in evaluation of durability of the drug coating layer using the imitative blood vessel. In FIG. 2, the axis of abscissas represents Examples or Comparative Examples, wherein numerals 1 to 7 mean Examples 1 to 7, respectively, and alphabet-accompanied numerals C1 to C4 mean Comparative Examples C1 to C4, respectively. Besides, the axis of ordinates represents the remaining rate of paclitaxel on the balloon after the delivery operation (unit: mass %). The "mass %" means "% by mass."

TABLE 4

| Examples/ Comparative examples | Amount of PTX coated on a balloon [µg/balloon] | Amount of PTX remaining on a balloon [µg/balloon] | Rates of PTX remaining on a balloon [mass %] |
|---|---|---|---|
| 1 | 306 | 284 | 93 |
| 2 | 278 | 225 | 81 |
| 3 | 290 | 209 | 72 |
| 4 | 343 | 243 | 71 |
| 5 | 294 | 212 | 72 |
| 6 | 285 | 200 | 70 |
| 7 | 333 | 257 | 77 |
| C1 | 322 | 106 | 33 |
| C2 | 367 | 187 | 51 |
| C3 | 343 | 171 | 50 |
| C4 | 492 | 227 | 46 |

In this evaluation system, in the case where the amount of the drug remaining on the balloon after the delivery operation is equal to or more than 60 mass %, the ability to hold the drug during the delivery operation is good, and much drug can be delivered to the affected part of a lesion. When the amount is below 60 mass %, on the other hand, much of the drug is peeled during the delivery operation, which is undesirable from the viewpoint of safety, as well. In this case, besides, the amount of drug that can be delivered to the affected part of a lesion is small, and, therefore, satisfactory transfer of the drug to the tissue cannot be expected. Accordingly, in this evaluation system, when the amount of paclitaxel remaining on the balloon after the delivery operation is equal to or more than 60 mass %, it can be judged that a good ability to hold the drug during the delivery process is secured.

As shown in Table 4, for the drug-eluting balloons fabricated in Examples 1 to 7, the amount of paclitaxel remaining on the balloon after the delivery operation was equal to or more than 60 mass % based on the coating amount. On the other hand, for the drug-eluting balloons fabricated in Comparative Examples C1 to C4, the amount of paclitaxel remaining on the balloon was equal to or less than 50 mass %. From the results above, it has been verified that the amino acid ester hydrochloride compounds having a hydropathy index of the amino acid of zero or less than zero which were used in Examples 1 to 7 ensures uniform coating with paclitaxel, enhances adhesion of paclitaxel to the balloon, and enhances the ability to hold the drug during the delivery operation. On the other hand, in the cases of the amino acid ester hydrochloride compounds having a hydropathy index of the amino acid of higher than 1 and being comparatively high in hydrophobicity, it was difficult to enhance the ability to hold the drug during the delivery operation. Besides, as shown in Comparative Example C3, in the case of an amino acid which has a hydropathy index of zero or less than zero, but is not esterified, a favorable drug durability performance could not be obtained.

Evaluation of Transferability of Drug to Tissue in Rabbit Iliac Artery

For the drug-eluting balloons in Example 8 and Comparative Examples C5 and C6, transferability of paclitaxel to blood vessel tissue after one hour from expansion of the balloon in a rabbit iliac artery was evaluated by the following procedure.

1. Method (1) A guide wire was inserted into a right iliac artery or a left iliac artery of a rabbit under radioscopic observation. Next, the drug-eluting balloon (having an expandable portion sized to be 3.0 mm in diameter and 20 mm in length when expanded) was transferred along the guide wire to the iliac artery.

(2) The balloon was expanded at 7 atm for one minute. Immediately thereafter, the balloon was pulled out.

(3) After 60 minutes from the expansion of the balloon, a blood vessel (a range of about 3.5 cm from branching) was sampled.

(4) Methanol was added to the sampled blood vessel, followed by homogenization, to obtain a tissue homogenate.

(5) The tissue homogenate was analyzed by high performance liquid chromatography, to determine the amount of paclitaxel contained in the tissue (the amount of paclitaxel per 1 g of tissue). Furthermore, from the amount of paclitaxel in the coating on the drug-eluting balloon and the amount of paclitaxel remaining on the balloon, the remaining rate of paclitaxel on the balloon (rate of PTX remaining on a balloon) was calculated.

2. Results

The results as set forth in Table 5 were obtained. In Table 5, 8 in the column of "Examples/Comparative examples" is Example 8, and C5 and C6 in the column are Comparative Examples. In Table 5, "Amount of PTX contained in tissue" represents the amount of paclitaxel contained in 1 g of blood vessel tissue (unit: µg/g tissue), "Rates of PTX transferred to tissue" represents the rates of paclitaxel transferred from the coating on the balloon into the blood vessel tissue (unit: mass %), and "Rates of PTX remaining on a balloon" represents the rates of paclitaxel remaining on the balloon (unit: mass %), respectively.

Figure 3:
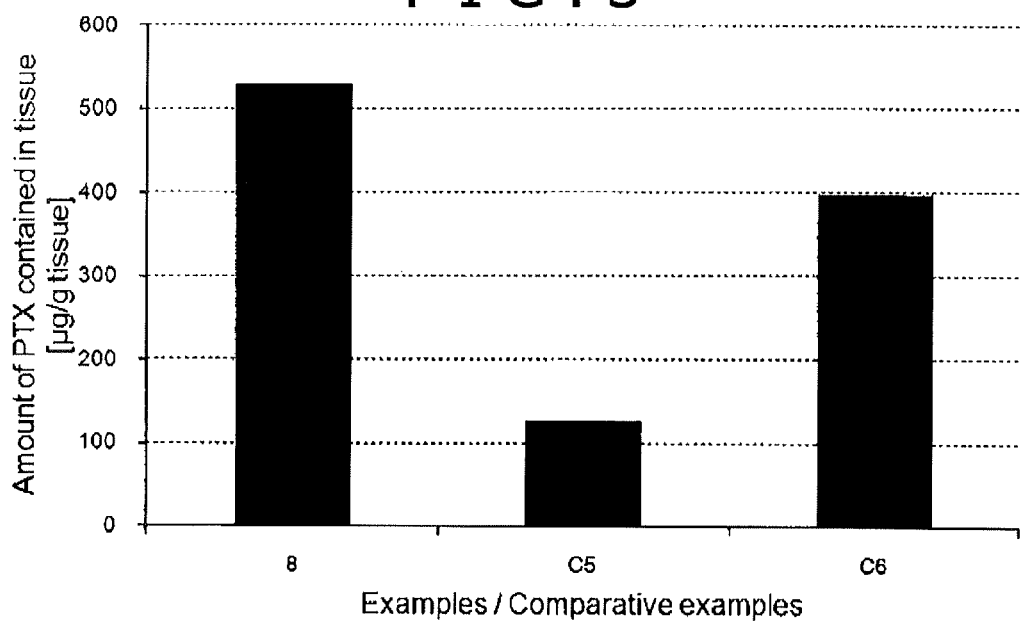
FIG. 3 is a graph representing the amount of paclitaxel contained in a blood vessel tissue in Example 8 and Comparative Examples C5 and C6, in an evaluation of the transferability of a drug to a tissue in a rabbit iliac artery.

In addition, FIG. 3 shows a graph representing the amount of paclitaxel contained in the blood vessel tissue in Example 8 and Comparative Examples C5 and C6, in the evaluation of transferability of the drug to the tissue in a rabbit iliac artery. In FIG. 3, the axis of abscissas represents Example or Comparative Examples, wherein numeral 8 means Example 8, and alphabet-accompanied numerals C5 and C6 mean Comparative Examples C5 and C6, respectively. Besides, the axis of ordinates represents the amount of paclitaxel contained in 1 g of blood vessel tissue (unit: µg/g tissue). The "µg/g tissue" means micrograms per gram of tissue.

TABLE 5

| Examples/ Comparative examples | Amount of PTX contained in tissue [µg/g tissue] | Rates of PTX transferred to tissue [mass %] | Rates of PTX remaining on a balloon [mass %] |
| --- | --- | --- | --- |
| 8 | 530.1 | 2.5 | 21.8 |
| C5 | 126.9 | 0.6 | 37.1 |
| C6 | 398.2 | 1.5 | 19.5 |

In Example 8, the amount of paclitaxel per unit area of balloon was 3.2 µg/mm$^2$, less than the value of 4.1 µg/mm$^2$ for the IN.PACT (produced by Invatec) in Comparative Example C6. As shown in Table 5 and FIG. 3, however, the amount of paclitaxel contained in the tissue recovered after 60 minutes from the expansion of the blood vessel was above 500 µg per 1 g of tissue, which value was more than the value for Comparative Example C6 and suggested favorable transfer of paclitaxel to the blood vessel tissue. On the other hand, in the case of the drug-eluting balloon in Comparative Example C5 where L-valine methyl ester (having a hydropathy index of the amino acid of 4.2) was used as the hydrophobic amino acid ester hydrochloride, the amount of paclitaxel remaining on the balloon was large, showing a low rate of transfer of paclitaxel to the blood vessel tissue. From the results above, it has been verified that paclitaxel present in the coating together with an amino acid ester hydrochloride having a hydropathy index of the amino acid of zero or less than zero shows efficient transfer of the drug to the tissue, that is, good transferability of drug.

Evaluation of Retention of Drug in Tissue in Rabbit Abdominal Aorta

For the drug-eluting balloons in Examples 9 and 10, the amount of paclitaxel contained in tissue after one hour and after 24 hours from expansion of the balloon in a rabbit abdominal aorta was determined, and the retention of drug was thereby evaluated, by the following procedure.

1. Method (1) The drug-eluting balloon was subjected to wrapping, followed by premounting of a stent thereon. The drug-eluting balloon with the stent premounted thereon was put to use.

(2) After a guide wire was inserted into an abdominal aorta of a rabbit under radioscopic observation, a guiding catheter was pulled out while holding the position of the guide wire. Next, the drug-eluting balloon (having an expandable portion sized to be 3.0 mm in diameter and 20 mm in length when expanded) with the stent premounted thereon was transferred along the guide wire to the abdominal aorta.

(3) The balloon was expanded at 7 atm for one minute. Immediately thereafter, the balloon was pulled out.

(4) After one hour and after 24 hours from the expansion of the balloon, a blood vessel (a range of about 3.5 cm from branching) was sampled.

(5) Methanol was added to the thus sampled blood vessel, followed by homogenization, to obtain a tissue homogenate.

(6) The tissue homogenate was analyzed by high performance liquid chromatography, to determine the amount of paclitaxel contained in the tissue (the amount of paclitaxel per 1 g of tissue) after one hour and after 24 hours from the expansion of the balloon. Furthermore, from the amount of paclitaxel present in the coating on the drug-eluting balloon and the amounts of paclitaxel contained in the tissue after one hour and after 24 hours from the expansion of the balloon, rates of transfer of paclitaxel to tissue (rates of PTX transferred to tissue) after one hour and after 24 hours from the expansion of the balloon were calculated, and the remaining rate (rate of PTX remaining on a balloon) was calculated from the amount of paclitaxel remaining on the balloon.

2. Results

The results as set forth in Table 6 were obtained. In Table 6, 9 and 10 in the column of "Examples" are Examples. Besides, in Table 6, "Amount of PTX contained in tissue" represents the amount of paclitaxel contained in 1 g of blood vessel tissue (unit: µg/g tissue), "Rates of PTX transferred to tissue" represents the rates of paclitaxel transferred from the coating on the balloon into the blood vessel tissue (unit: mass %), and "Rates of PTX remaining on a balloon" represents the rates of paclitaxel remaining on the balloon (unit: mass %). Furthermore, "1H" and "24H" in the columns of "Amount of PTX contained in tissue" and "Rates of PTX transferred to tissue" mean one hour after the expansion of blood vessel lumen and 24 hours after the expansion of blood vessel lumen, respectively.

Figure 4:
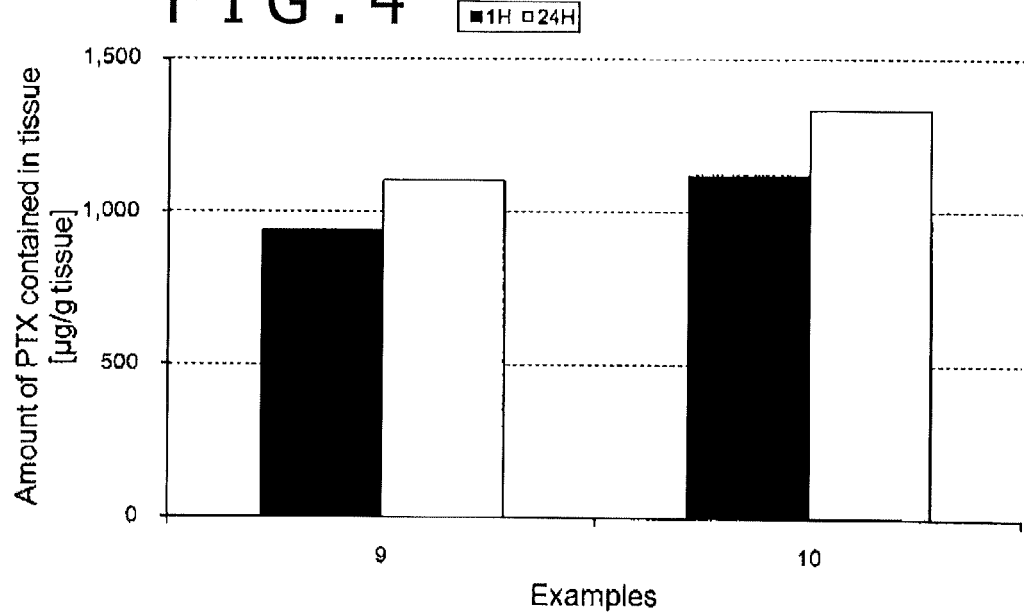
FIG. 4 is a graph representing the amount of paclitaxel remaining in a blood vessel tissue after one hour and after 24 hours from expansion of the blood vessel lumen in Examples 9 and 10, in an evaluation of the retention of a drug in a tissue in a rabbit abdominal aorta.

FIG. 4 shows a graph representing the amount of paclitaxel remaining in the blood vessel tissue after one hour and after 24 hours from the expansion of the blood vessel lumen in Examples 9 and 10, in evaluation of retention of drug in tissue in a rabbit abdominal aorta. In FIG. 4, the axis of abscissas represents Examples, wherein numerals 9 and 10 mean Examples 9 and 10, respectively. The axis of ordinates represents the amount of paclitaxel contained in 1 g of blood vessel tissue (unit: μg/g tissue). In the legend, "1H" and "24H" mean one hour after the expansion of blood vessel lumen and 24 hours after the expansion of blood vessel lumen, respectively. The "μg/g tissue" means "micrograms per gram of tissue."

TABLE 6

| Examples | Amount of PTX contained in tissue [μg/g tissue] | | Rates of PTX transferred to tissue [mass %] | | Rates of PTX remaining on a balloon [mass %] |
|---|---|---|---|---|---|
| | 1 H | 24 H | 1 H | 24 H | |
| 9 | 945.0 | 1106.1 | 5.6 | 5.1 | 10.4 |
| 10 | 1126.4 | 1338.9 | 4.9 | 7.1 | 8.2 |

As shown in Table 6, in Examples 9 and 10, the amounts of paclitaxel contained in the blood vessel tissue after one hour and after 24 hours from the expansion of the blood vessel had approximately equal values, suggesting that the amount of paclitaxel in the blood vessel tissue does not attenuate largely with the lapse of time. From the results above, it has been verified that a drug coating layer containing an amino acid ester hydrochloride having a hydropathy index of the amino acid of zero or less than zero (specifically, hydrochloride of L-serine ethyl ester, having a hydropathy index of the amino acid of −0.8) and paclitaxel ensures that a sufficient amount of the drug is retained in the tissue for a long period of time, after the transfer of the drug to the tissue. When glycerine is contained in the drug coating layer, also, a sufficient retention of drug in tissue can be obtained.

Evaluation of Effectiveness in Swine Coronary Artery

For the drug-eluting balloons in Examples 9 to 11 and Comparative Example C6 as well as the non-drug-coated balloon in Comparative Example C7, the effectiveness in a swine coronary artery was evaluated by the following procedure.

1. Method (1) A guiding catheter was inserted via an 8 Fr. sheath, together with a guide wire, and was guided to left and right coronary artery orifices of a swine under radioscopic observation.

(2) Angiography was applied to each coronary artery (coronary artery: left anterior descending coronary artery (LAD), right coronary artery (RCA), left circumflex coronary artery (LCX)), and the blood vessel diameter of the coronary artery obtained by the angiography was measured by a QCA software.

(3) A part where the diameter of the stent is 1.2 times the blood vessel diameter and the diameter of the drug-eluting balloon is 1.3 times the blood vessel diameter was selected, and operations from a stent placement operation were carried out there.

(4) The stent (stent sized to be 3 mm in diameter and 15 mm in length) was expanded to 1.2 times in size in the selected coronary artery for 30 seconds, and then a balloon catheter for placing the stent indwelling was pulled out. In the stent indwelling site, the drug-eluting balloon (balloon sized to be 3 mm in diameter and 20 mm in length) was expanded to a diameter of 1.3 times the blood vessel diameter for one minute, and then the catheter was pulled out.

(5) After the expansion of the drug-eluting balloon was over, the guiding catheter and the sheath were pulled out, and the central side of the carotid artery was ligated. Thereafter, at an external opening of wound of a cervical part, the dissected muscles were sutured with a surgical suture, and skins were sutured with a skin-suturing stapler.

(6) After 28 days from the expansion of the balloon, autopsy was conducted. At the time of the autopsy, coronary angiography was conducted, whereby the patency (stenosis rate) in the stent indwelling site was checked, and the blood vessel diameter was measured. The stenosis rate (%) was calculated from the average blood vessel diameter immediately after balloon expansion and the average blood vessel diameter after 28 days.

2. Results

The results as set forth in Table 7 were obtained. In Table 7, 9 to 11 in the column of "Examples/Comparative examples" are Examples, and C6 and C7 in the column are Comparative Examples.

FIG. 5 shows a graph representing blood vessel stenosis rate in Examples 9 to 11 and Comparative Examples C6 and C7, in evaluation of effectiveness in a swine coronary artery. In FIG. 5, the axis of abscissas represents Examples or Comparative Examples, wherein numerals 9 to 11 mean Examples 9 to 11, respectively, whereas alphabet-accompanied numerals C6 and C7 mean Comparative Examples C6 and C7, respectively. Besides, the axis of ordinates represents blood vessel stenosis rate (unit: %).

TABLE 7

| Examples/ Comparative examples | Stenosis rate [%] | S.D. |
|---|---|---|
| 9 | 16.1 | 6.88 |
| 10 | 6.5 | 10.82 |
| 11 | 7.3 | 2.68 |
| C6 | 17.1 | 5.48 |
| C7 | 35.0 | 14.28 |

The stenosis rate of a blood vessel treated with the non-drug-coated balloon prepared as a non-drug-treated control in Comparative Example C7 was 35.0%. Besides, the stenosis rate of a blood vessel treated with the commercialized drug-eluting balloon (IN.PACT) prepared in Comparative Example C6 was 17.1%.

On the other hand, the stenosis rates of blood vessels treated with the drug-eluting balloons fabricated in Examples 9 to 11 were 16.1%, 6.5%, and 7.3%, respectively.

From the results above, it has been verified that a drug coating layer containing an amino acid ester hydrochloride having a hydropathy index of the amino acid of zero or less than zero (and glycerine) and paclitaxel shows a good stenosis-restraining or suppressing effect.

When a medical device (for example, balloon catheter) coated with the coating composition according to the disclosed aspects is used, a drug can be efficiently delivered to the affected part of a lesion while restraining or suppressing separation of the drug coating layer from the medical device during the process of delivery to the affected part of the lesion. In addition, rapid release of the drug from the medical device at the affected part of the lesion can be promoted, and transferability of the drug to the tissue can be enhanced.

The detailed description above describes a coating composition for a drug-eluting medical device disclosed by way of examples. The invention is not limited, however, to the precise embodiments and variations described. Various changes, modifications and equivalents can implemented by one skilled in the art without departing from the spirit and scope of the invention as defined in the accompanying claims. It is expressly intended that all such changes, modifications and equivalents which fall within the scope of the claims are embraced by the claims.

What is claimed is:

1. A coating composition for a drug-eluting medical device, containing a water-insoluble drug and at least one selected from the group consisting of ester compounds of amino acids, which have a hydrophobicity index of the amino acid of zero or less than zero, and salts thereof, wherein the ester compound is an ester compound of at least one amino acid and a monohydric alcohol of up to five carbon atoms, and
   wherein the coating composition contains the ester compounds and/or the salts thereof in a total amount of 5 to 200 parts by weight based on 100 parts by weight of the water-insoluble drug.

2. The coating composition according to claim 1, wherein the amino acid is an α-amino acid.

3. The coating composition according to claim 1, wherein the at least one amino acid is selected from the group consisting of glycine, serine, asparagine, aspartic acid, glutamine, glutamic acid, arginine, threonine, histidine, lysine, tyrosine, tryptophan, amino acids obtained by replacing at least one of hydrogen atoms of an amino group at α-position in the above-mentioned amino acids with an alkyl group of up to five carbon atoms, a benzyl group or a benzoyl group, proline and amino acids obtained by replacing a hydrogen atom of an imino group of proline with an alkyl group of up to five carbon atoms, a benzyl group or a benzoyl group.

4. The coating composition according to claim 1, wherein the ester compound is represented by the following formula:

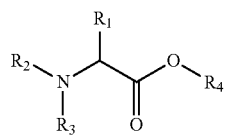

where $R_1$ is a hydrogen atom, guanidinopropyl group, carbamoylmethyl group, carboxymethyl group, methoxycarbonylmethyl group, ethoxycarbonylmethyl group, 2-carbamoyl-ethyl group, 2-carboxyethyl group, 2-methoxycarbonylethyl group, 2-ethoxycarbonylethyl group, (1H-imidazol-4-yl)methyl group, 4-aminobutyl group, hydroxymethyl group, 1-hydroxyethyl group, (1H-indol-3-yl)methyl group or 4-hydroxybenzyl group or forms a trimethylene group together with $R_2$, $R_2$ is a hydrogen atom or forms a trimethylene group together with $R_1$, $R_3$ is a hydrogen atom, an alkyl group of up to five carbon atoms, benzyl group or benzoyl group, and $R_4$ is an alkyl group of up to five carbon atoms.

5. The coating composition according to claim 1, wherein the ester compound is at least one selected from the group consisting of benzylglycine ethyl ester, benzylglycine methyl ester, arginine ethyl ester, arginine methyl ester, benzoylarginine ethyl ester, benzoylarginine methyl ester, diethyl aspartate, methyl aspartate, dimethyl aspartate, glycine ethyl ester, glycine methyl ester, serine ethyl ester and serine methyl ester.

6. The coating composition according to claim 1, further containing a lower alcohol.

7. The coating composition according to claim 6, wherein the lower alcohol is glycerine.

8. The coating composition according to claim 1, wherein the water-insoluble drug is at least one selected from the group consisting of paclitaxel, rapamycin, docetaxel and everolimus.

9. A drug coating layer which is formed on at least part of a surface of a medical device by use of the coating composition according to claim 1.

10. A drug-eluting medical device having an outer surface coated with the coating composition according to claim 1.

11. The drug-eluting medical device according to claim 10,
    wherein the medical device is a medical device which is radially expandable in a lumen.

12. The drug-eluting medical device according to claim 11,
    wherein the medical device which is radically expandable in the lumen is a balloon catheter or a stent.

13. A method of treatment comprising:
    a step of delivering the medical device according to claim 10 into a lumen;
    a step of radially expanding the medical device in the lumen; and
    a step of eluting a drug from a drug coating layer formed on at least part of the surface of the medical device, and allowing the drug to act on the lumen.

14. A method of treatment comprising:
    a step of delivering the medical device according to claim 11 into a lumen;
    a step of radially expanding the medical device in the lumen; and
    a step of eluting a drug from a drug coating layer formed on at least part of the surface of the medical device, and allowing the drug to act on the lumen.

15. A method of treatment comprising:
    a step of delivering the medical device according to claim 12 into a lumen;
    a step of radially expanding the medical device in the lumen; and
    a step of eluting a drug from a drug coating layer formed on at least part of the surface of the medical device, and allowing the drug to act on the lumen.

* * * * *